United States Patent
Zierke et al.

[11] Patent Number: 5,174,997
[45] Date of Patent: Dec. 29, 1992

[54] 3-SUBSTITUTED PYRIDINEMETHANOLS, AND FUNGICIDES CONTAINING SAME

[75] Inventors: Thomas Zierke, Boehl-Iggelheim; Thomas Kuekenhoehner, Frankenthal; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 645,242

[22] Filed: Jan. 24, 1991

[30] Foreign Application Priority Data

Feb. 13, 1990 [DE] Fed. Rep. of Germany ....... 4004317

[51] Int. Cl.$^5$ .................... A01N 25/14; A01N 43/40
[52] U.S. Cl. .................................. 424/405; 424/409; 514/277; 546/344
[58] Field of Search ............... 424/409, 405; 514/240, 514/277; 546/344

[56] References Cited

U.S. PATENT DOCUMENTS

| | | | |
|---|---|---|---|
| 3,335,148 | 8/1967 | Krumkalns et al. | 260/297 |
| 3,396,224 | 8/1968 | Van Heyningen | 424/263 |
| 4,431,812 | 2/1984 | Buschmann et al. | 546/344 |

FOREIGN PATENT DOCUMENTS

| | | |
|---|---|---|
| 0359077 | 3/1990 | European Pat. Off. |
| 1595261 | 8/1989 | United Kingdom |
| 2219793 | 12/1989 | United Kingdom |

OTHER PUBLICATIONS

CA: 90:82136u, vol. 90, 1979.
CA 98:198037g, vol. 98, 1983.
CA 75:151680w, vol. 75, 1971.

Primary Examiner—Thurman K. Page
Assistant Examiner—Neil S. Levy
Attorney, Agent, or Firm—Oblon, Spivak, McClelland, Maier & Neustadt

[57] ABSTRACT

Compounds of the formula 1

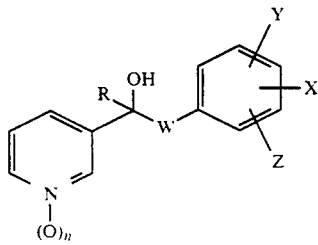

where
R is unsubstituted or substituted cycloalkyl or cycloalkenyl,
X, Y and Z are hydrogen, halogen, alkyl, alkoxy, alkoximino, haloalkyl, cyano, nitro or unsubstituted or substituted phenyl or phenoxy,
W is —CH$_2$— or —CH$_2$CH$_2$— and
n is 0 or 1, and the plant-tolerated acid-addition salts thereof, and fungicides containing these compounds are described.

8 Claims, No Drawings

3-SUBSTITUTED PYRIDINEMETHANOLS, AND FUNGICIDES CONTAINING SAME

The present invention relates to novel 3-pyridinemethanols, to fungicides which contain the novel active ingredients, and to a method of combating fungi using these active ingredients.

It is known to use 3-pyridinemethanols as fungicides. For example, U.S. Pat. No. 3,396,224 discloses alpha-(4-chlorophenyl)-alpha-cyclopropyl-3-pyridinemethanol as a fungicidal compound. However, the fungicidal action of this compound is frequently inadequate, in particular at low application rates.

It is therefore an object of the present invention to find novel 3-pyridinemethanols which have a different chemical structure and a fungicidal action superior to the conventional 3-pyridinemethanols.

We have found that this object is achieved by 3-pyridinemethanols of the formula 1

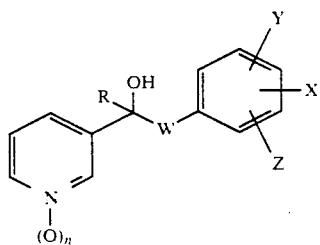

where
R is unsubstituted or $C_1$-$C_4$-alkyl-substituted $C_3$-$C_8$-cycloalkyl, or unsubstituted or $C_1$-$C_4$-alkyl-substituted $C_3$-$C_8$-cycloalkenyl, X, Y and Z, independently of one another, are hydrogen, halogen, $C_1$-$C_4$-alkyl, $C_1$-$C_4$-alkoxy, $C_1$-$C_4$-alkoximino, halo-$C_1$-$C_4$-alkyl, cyano, nitro, unsubstituted or halogen-substituted phenyl, or unsubstituted or halogen-substituted phenoxy, W is —$CH_2$— or —$CH_2CH_2$—, and
n is 0 or 1,
and the plant-compatible acid-addition salts thereof, which have a surprisingly better fungicidal action than the 3-pyridinemethanols known from U.S. Pat. No. 3,396,224.

R is, for example, cyclopropyl, cyclobutyl, cyclopentyl, cyclohexyl, cycloheptyl, cyclooctyl, 1-methylcyclopropyl, 1-ethylcyclopropyl, 1-methylcyclopentyl, 4-methylcyclohexyl, 4-isopropylcyclohexyl, 4-tert-butylcyclohexyl, 2-methylcyclopentyl or 2-methylcyclohexyl.

Through substituents X, Y and Z and the phenyl ring, the invention covers unsubstituted, monosubstituted, disubstituted or trisubstituted phenyl rings, e.g. phenyl, halophenyl, 4-chlorophenyl, 4-fluorophenyl, 4-bromophenyl, 2-chlorophenyl, 2-fluorophenyl, 2-bromophenyl, 2,4-dichlorophenyl, 2-bromo-4-chlorophenyl, 2-chloro-4-bromophenyl, 2-chloro-4-fluorophenyl, 2,3-dichlorophenyl, 2-chloro-3-fluorophenyl, 2-fluoro-4-chlorophenyl, 2-chloro-3-fluoro-4-chlorophenyl, 2-bromo-4-fluorophenyl, 2-bromo-3-fluoro-4-chlorophenyl, 2,6-dichlorophenyl, 2-trifluoromethylphenyl, 4-trifluoromethylphenyl, $C_1$-$C_4$-alkylphenyl, 2-methylphenyl, 4-methylphenyl, 4-tert.-butylphenyl, 2-chloro-4-methylphenyl, 2-methyl-4-chlorophenyl, 2,4-dimethylphenyl, 2,3-dimethylphenyl, $C_1$-$C_4$-alkoxyphenyl, 2-methoxyphenyl, 4-methoxyphenyl, 2-chloro-4-methoxyphenyl, 2-methyl-4-methoxyphenyl, 4-tert.-butoxyphenyl, $C_1$-$C_4$-alkoximinophenyl, 4-methoximinophenyl, 4-ethoximinophenyl, 2-chloro-4-methoximinophenyl, 4-cyanophenyl, 2-chloro-4-cyanophenyl, 2-cyano-4-chlorophenyl, 2-cyanophenyl, 2-nitrophenyl, 4-nitrophenyl, 2-chloro-4-nitrophenyl, halophenoxyphenyl, 4-phenoxyphenyl and 4-(4'-chlorophenoxy)phenyl.

Examples of salts which are compatible with plants are acid-addition salts with inorganic mineral acids, such as hydrochlorides, hydrobromides, sulfates, phosphates and nitrates, salts with formic acid or with alkylcarboxylic acids, such as acetates, 2-ethylhexanoates and oxalates, salts with arylsulfonic acids, such as benzenesulfonates, toluenesulfonates and dodecylbenzenesulfonates.

The novel compounds of the formula 1 generally contain chiral carbon atoms. They are generally obtained as racemates or possibly as diastereomer mixtures. Diastereomerically pure compounds can be isolated in the case of some of the novel compounds by distillation, column chromatography or on the basis of solubility differences. Enantiomerically pure compounds can be obtained, for example, by resolving the racemates by known methods using chiral auxiliary reagents or via diastereomeric salts. The diastereomers and the enantiomers and the stereoisomer mixtures produced in the synthesis are suitable for use of the novel compounds as fungicides. All these are covered by the invention.

Compounds of the formula 1 in which n is 1 are obtained by treating the corresponding compounds of the formula I where n is 0 with a peracid or with a mixture of an acid, such as acetic acid, and hydrogen peroxide.

The preparation processes for compounds of the formula 1 where n is 0 are illustrated by the reaction equations below:

Eq. 1:

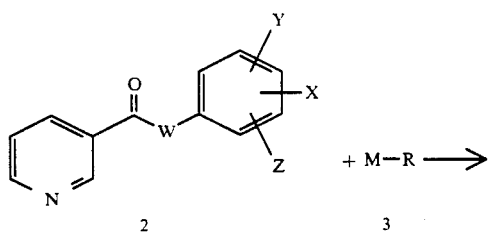

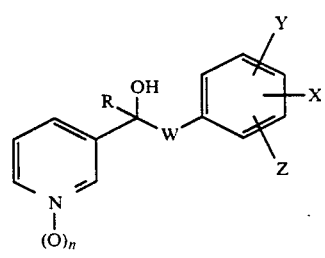

Eq. 2:

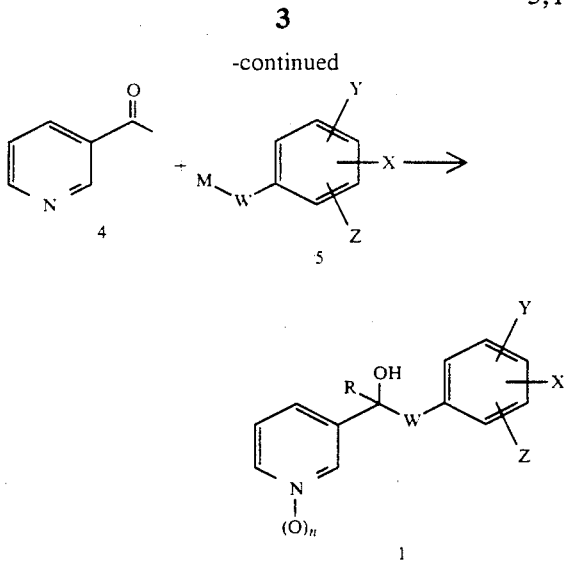

In the formulae 2 to 5, W, X, Y, Z and R are as defined for formula 1. In the formulae 3 and 5, M may be lithium, sodium, potassium, MgCl or MgBr. Reactions with organometallic agents, as illustrated by equations 1 and 2, are conventional reactions of organic chemistry (see, for example, Organikum, 15th edition, 1977, pp. 623 ff.). The reaction is expediently carried out by metering the ketone component into from 1 to 2 equivalents of the organometallic compound in an inert solvent, preferably diethyl ether, methyl tert-butyl ether, tetrahydrofuran or a mixture thereof, at from $-50°$ C. to $+50°$ C.

Ketones of the formulae 2 and 4 are conventional compounds and can be prepared by a variety of conventional methods. An example of a preferred method is to alkylate alpha-morpholino-3-pyridylacetonitrile using an alkylating agent of the formula 6 or 7, and then to liberate the ketone function (E. Leete et al., JOC 37 (1972), 4465) or to carry out the addition reaction of 3-pyridyllithium (W. E. Parham et al., JOC 42 (1977), 257 ff.) with an aldehyde of the formula 8 or 9, and then to oxidize the resultant carbinol.

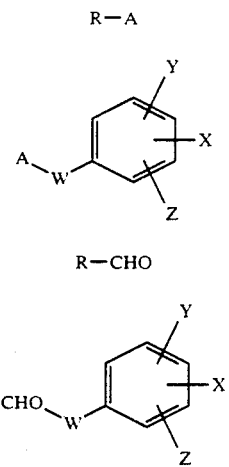

In the formulae 6 to 9, W, X, Y, Z and R are as defined for formula 1. A is a group which can be substituted nucleophilically, e.g. chlorine, bromine, iodine, tosylate, benzenesulfonate or mesylate.

The examples below describe the preparation of the novel compounds.

EXAMPLE 1

Alpha-cyclopropyl-alpha-(2,4-dichlorobenzyl)-3-pyridylcarbinol (Compound No. 1)

2 g (0.014 mol) of 3-pyridyl cyclopropyl ketone, dissolved in 10 ml of tetrahydrofuran (THF), are added dropwise to a solution of 2,4-dichlorobenzylmagnesium chloride (prepared from 0.66 g (0.027 mol) of magnesium turnings and 5.3 g (0.027 mol) of 2,4-dichlorobenzyl chloride) in 20 ml of diethyl ether (Et$_2$O). The mixture is left at room temperature (20° C.) for 1 hour, saturated NH$_4$Cl solution is added, and the mixture is worked up. The aqueous phase is extracted once with methylene chloride (CH$_2$Cl$_2$). The combined organic phases are dried over Na$_2$SO$_4$ and filtered, and the filtrate is evaporated to give colorless crystals.

Yield: 1.48 g (35%), melting point: 98°–100° C.

$^1$H-NMR (CDCl$_3$/TMS$_{int}$): δ/ppm=0.2–0.6 (m, 4H), 1.35–1.5 (m, 1H), 2.25 (s, broad, 1H), 3.2 (d, 1H), 3.4 (d, 1H), 6.9–7.4 (m, 4H), 7.7 (d, 1H), 8.45 (d, 1H), 8.7 (s, 1H).

EXAMPLE 2

Preparation of α-cyclohexyl-α-(4-fluorophenethyl)-3-pyridylcarbinol (Compound No. 29)

6 g (0.026 mol) of 1-(pyrid-3-yl)-3-(4-fluorophenyl)-propanone, dissolved in 10 ml of tetrahydrofuran (THF), are added dropwise to a solution of cyclohexylmagnesium bromide (prepared from 0.7 g (0.03 mol) of magnesium turnings and 4.7 g (0.03 mol) of cyclohexyl bromide) in 20 ml of diethyl ether (Et$_2$O). The mixture is allowed to react for 5 hours at room temperature (20° C.), saturated NH$_4$Cl solution is added, and the mixture is worked up. The aqueous phase is extracted once with methylene chloride (CH$_2$Cl$_2$). The combined organic phases are dried over Na$_2$SO$_4$ and filtered, and the filtrate is evaporated. The oil which remains is chromatographed on silica gel (eluent: cyclohexane/ethyl acetate 50/50). A pale yellow oil is obtained.

Yield: 1.9 g (23%)

$^1$H-NMR (CDCl$_3$/TMS$_{int}$): Δ/ppm=0.85 (m, 15H), 2.48–2.67 (m, 1H), 6.8–7.1 (m, 4H), 7.22–35 (m, 1H), 7.7–8 (m, 1H), 8.5 (d, 1H), 8.7 (s, 1H)

The following compounds of the general formula 1 according to the invention

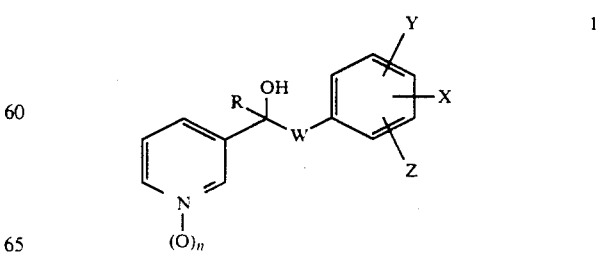

where n is 0, can be prepared in a corresponding manner:

n = 0

| No. | W | R | | Physical data |
|---|---|---|---|---|
| 1 | —CH$_2$— | cyclopropyl | 2,4-Dichlorophenyl | 98–100° C. |
| 2 | —CH$_2$— | cyclopropyl | Phenyl | Oil. NMR: 3.25(s, 2H) |
| 3 | —CH$_2$— | cyclopropyl | 4-Fluorophenyl | Oil. NMR: 3.2(s, 2H) |
| 4 | —CH$_2$— | cyclopropyl | 4-Chlorophenyl | Oil. NMR: 3.15(s, 2H) |
| 5 | —CH$_2$— | cyclopropyl | 2-Chlorophenyl | Oil. NMR: 3.25(d, 1H), 3.5(d, 1H) |
| 6 | —CH$_2$— | cyclopropyl | 4-Methylphenyl | Oil. NMR: 2.28(s, 2H) |
| 7 | —CH$_2$CH$_2$— | cyclopropyl | 4-Fluorophenyl | Oil. NMR: 2.0–2.28(m, 2H), 2.3–2.48(m, 1H), 2.6–2.8(m, 1H) |
| 8 | —CH$_2$— | cyclopropyl | 2,4-Dimethylphenyl | |
| 9 | —CH$_2$— | cyclopropyl | 2,3-Dichlorophenyl | |
| 10 | —CH$_2$— | cyclopropyl | 3,4-Dichlorophenyl | |
| 11 | —CH$_2$— | cyclopropyl | 2-Chloro-4-fluorophenyl | |
| 12 | —CH$_2$— | cyclopropyl | 2-Bromo-4-fluorophenyl | |
| 13 | —CH$_2$— | cyclopropyl | 4-Cyanophenyl | |
| 14 | —CH$_2$— | cyclopropyl | 4-Methoximinophenyl | |
| 15 | —CH$_2$— | cyclopropyl | 2-Bromophenyl | |
| 16 | —CH$_2$— | cyclopropyl | 2-Chloro-4-methylphenyl | |
| 17 | —CH$_2$— | cyclopropyl | 2-Trifluoromethylphenyl | |
| 18 | —CH$_2$— | cyclopropyl | 3-Trifluoromethylphenyl | |
| 19 | —CH$_2$— | cyclopropyl | 2-Chloro-4-methoxyphenyl | |
| 20 | —CH$_2$— | cyclopropyl | 4-Methoxyphenyl | |
| 21 | —CH$_2$— | cyclopropyl | 4-tert.-Butylphenyl | |
| 22 | —CH$_2$— | cyclopropyl | 2-Fluorophenyl | |
| 23 | —CH$_2$— | cyclopropyl | 4-Phenoxyphenyl | |
| 24 | —CH$_2$— | cyclopropyl | 2-Fluoro-4-chlorophenyl | |
| 25 | —CH$_2$— | cyclopropyl | 2,4-Dichloro-3-fluorophenyl | |
| 26 | —CH$_2$— | cyclopentyl | 2,4-Dichlorophenyl | Oil. NMR: 1.1–2.0(m, 9H), 2.7(p, 1H), 3.1(d, 2H), 3.3(d, 1H) |
| 27 | —CH$_2$— | cyclopentyl | 4-Fluorophenyl | Oil. NMR: 1.1–2.0(m, 9H), 2.5(p, 1H), 3.1(s, 2H) |
| 28 | —CH$_2$CH$_2$— | cyclopentyl | 4-Fluorophenyl | Oil. NMR: 1.4–2.65(m, 14H) |
| 29 | —CH$_2$CH$_2$— | cyclohexyl | 4-Fluorophenyl | Oil. NMR: 0.85–2.32(m, 15H), 2.48–67(m, 1H) |
| 30 | —CH$_2$— | cyclohexyl | 2,4-Dichlorophenyl | m.p. 65° C. |
| 31 | —CH$_2$— | cyclobutyl | 2,4-Dichlorophenyl | |
| 32 | —CH$_2$— | 1-methylcyclopropyl | | |
| 33 | —CH$_2$— | 4-methylcyclohexyl | 2,4-Dichlorophenyl | |
| 34 | —CH$_2$— | cycloheptyl | 4-Fluorophenyl | |
| 35 | —CH$_2$— | cyclooctyl | 4-Fluorophenyl | |
| 36 | —CH$_2$— | cyclohexyl | 2-Chloro-4-methylphenyl | |
| 37 | —CH$_2$— | cyclohexyl | 2,4-Dimethylphenyl | |
| 38 | —CH$_2$— | cyclohexyl | 2-Chlorophenyl | Oil. NMR: 0.9–2.27(m, 12H), 3.2(d, 1H), 3.7(d, 1H) |
| 39 | —CH$_2$— | cyclohexyl | 2-Bromophenyl | |
| 40 | —CH$_2$— | cyclohexyl | 2-Chloro-4-fluorophenyl | |
| 41 | —CH$_2$— | cyclohexyl | 2-Bromo-4-fluorophenyl | |
| 42 | —CH$_2$— | cyclopentyl | 2-Chloro-4-methylphenyl | |
| 43 | —CH$_2$— | cyclopentyl | 2,4-Dimethylphenyl | |
| 44 | —CH$_2$— | cyclopentyl | 2-Chlorophenyl | Oil. NMR: 1.0–2.0(m, 9H), 2.65(p, 1H), 3.25(dd, 2H) |
| 45 | —CH$_2$— | cyclopentyl | 2-Bromophenyl | |
| 46 | —CH$_2$— | cyclopentyl | 2-Chloro-4-fluorophenyl | |
| 47 | —CH$_2$— | cyclopentyl | 2-Bromo-4-fluorophenyl | |
| 48 | —CH$_2$— | cyclopentyl | 2-Fluoro-4-chlorophenyl | |
| 49 | —CH$_2$— | cyclopentyl | 2,3-Dichlorophenyl | |
| 50 | —CH$_2$— | cyclohexyl | 2,3-Dichlorophenyl | |
| 51 | —CH$_2$CH$_2$— | cyclopropyl | 4-Chlorophenyl | |
| 52 | —CH$_2$CH$_2$— | cyclopentyl | 4-Chlorophenyl | |
| 53 | —CH$_2$CH$_2$— | cyclohexyl | 4-Chlorophenyl | |
| 54 | —CH$_2$CH$_2$— | cyclopropyl | 2,4-Dichlorophenyl | |
| 55 | —CH$_2$CH$_2$— | cyclopropyl | Phenyl | |
| 56 | —CH$_2$CH$_2$— | cyclopropyl | 4-Methylphenyl | |
| 57 | —CH$_2$CH$_2$— | cyclopropyl | 2,4-Dimethylphenyl | |
| 58 | —CH$_2$CH$_2$— | cyclopentyl | 2,4-Dichlorophenyl | |
| 59 | —CH$_2$CH$_2$— | cyclohexyl | 4-Methylphenyl | |
| 60 | —CH$_2$CH$_2$— | cyclopentyl | 2,4-Dimethylphenyl | |
| 61 | —CH$_2$CH$_2$— | cyclohex-2-en-1-yl | 4-Fluorophenyl | |
| 62 | —CH$_2$CH$_2$— | cyclohex-2-en-1-yl | 4-Chlorophenyl | |
| 63 | —CH$_2$— | cyclopentyl | 4-Chlorophenyl | Oil. NMR: 1.15–2.0(m, 9H), 2.52(p, 1H), 3.12(s, 2H) |
| 64 | —CH$_2$— | cyclohexyl | 4-Chlorophenyl | Oil. NMR: 0.8–2.15(m, 12H), 3.12(d, 1H), 3.25(d, 1H) |
| 65 | —CH$_2$— | cyclohexyl | 4-Fluorophenyl | Oil. NMR: 3.15(d, 1H), 3.25(d, 1H) |

Compounds of the formula 1 in which n is 1 can be prepared from the compounds of the table by treatment with a peracid, such as meta-chloroperbenzoic acid or peracetic acid, and subsequently separating off the resultant carboxylic acid by washing with aqueous NaHCO$_3$ solution. This synthesis is illustrated by the following preparation procedure as an example of the preparation of the N-oxide of compound 1 in the table:

EXAMPLE 3

α-Cyclopropyl-α-(2,4-dichlorobenzyl)-3-pyridylcarbinol N-oxide 3 g (0.01 mol) of α-cyclopropyl-α-(2,4-dichlorobenzyl)-3-pyridylcarbinol (compound No. 1) are added to 2.4 g (0.011 mol) of meta-chlorobenzoic acid in 150 ml of methylene chloride ($CH_2Cl_2$). The mixture is left to stand overnight at room temperature, the meta-chlorobenzoic acid is filtered off, and the mixture is washed with $NaHCO_3$ solution and $NaHSO_3$ solution and dried over $Na_2SO_4$. Evaporation gives an oil which is chromatographed on silica gel (eluent: cyclohexane/ethyl acetate 50/50), to give pale brown crystals.

Yield: 0.8 g (25%), melting point: 69°-73° C.

$^1$H-NMR ($CDCl_3$/$TMS_{int}$): δ/ppm=0.27-60 (m, 4H), 1.22-40 (m, 1H), 3.15 (d, 2H), 3.35 (d, 2H), 4.05-60 (s, broad, 1H), 7.0-4 (m, 5H), 8.0 (d, 1H), 8.32 (s, 1H).

The novel compounds have in general excellent activity against a broad spectrum of phytopathogenic fungi, in particular from the class consisting of the Ascomycetes and Basidiomycetes. Some of them have systemic activity and can be used as foliage or soil fungicides.

They are of particular interest for controlling a large number of fungi on various crops or their seeds, in particular wheat, rye, barley, oats, rice, corn, lawns, cotton, soybean, coffee, sugar cane, fruit and ornamentals in horticulture, in viticulture and on vegetables, such as cucumbers, beans and cucurbitaceae.

The novel compounds are particularly suitable for controlling the following plant diseases:

*Erysiphe graminis* (powdery mildew) in cereals,
*Erysiphe cichoracearum* and *Sphaerotheca fuliginea* in cucurbitaceae,
*Podosphaera leucotricha* in apples,
*Uncinula necator* on grapevines,
Puccinia species on cereals,
Rhizoctonia species on cotton and lawns,
Ustilago species on cereals and sugar cane,
*Venturia inaequalis* (scab) on apples,
Helminthosporium species on cereals,
*Septoria nodorum* on wheat,
*Botrytis cinerea* (gray mold) on strawberries and grapevines,
*Cercospora arachidicola* on peanuts,
*Pseudocercosporella herpotrichoides* on wheat and barley,
*Pyricularia oryzae* on rice,
*Phytophthora infestans* on potatoes and tomatoes,
Fusarium and Verticillium species on various plants,
*Plasmopara viticola* on grapevines and
Alternaria species on vegetables and fruit.

The compounds are used by spraying or dusting the plants with the active ingredients or treating the seeds of the plants with the active ingredients. Application is effected before or after infection of the plants or seeds with the fungi. The fungi or the plants, seed, materials or soil to be protected against fungal attack are treated with an effective amount of the active ingredient.

The novel substances can be converted into the conventional formulations such as solutions, emulsions, suspensions, dusts, powders, pastes and granules. The application forms depend entirely on the intended uses; they should in any case ensure a fine and uniform distribution of the active substance. The formulations are prepared in a known manner, for example by extending the active ingredient with solvents and/or carriers, if necessary with the use of emulsifiers and dispersants, it also being possible to use other organic solvents as auxiliary solvents when water is used as the diluent. Suitable assistants for this purpose are essentially solvents, such as aromatics (e.g. xylene), chlorinated aromatics (e.g. chlorobenzenes), paraffins (e.g. mineral oil fractions), alcohols (e.g. methanol or butanol), ketones (e.g. cyclohexanone), amines (e.g. ethanolamine or dimethylformamide) and water; carriers, such as ground natural minerals (e.g. kaolins, clays, talc or chalk) and ground synthetic minerals (e.g. finely divided silica or silicates); emulsifiers, such as nonionic and anionic emulsifiers (e.g. polyoxyethylene fatty alcohol ethers, alkylsulfonates and arylsulfonates) and dispersants, such as ligninsulfite waste liquors and methylcellulose.

The fungicides generally contain from 0.1 to 95% by weight, preferably from 0.5 to 90% by weight of active ingredient.

The application rates are from 0.02 to 3 kg or more of active ingredient per ha, depending on the type of effect desired. The novel compounds can also be employed in materials protection (wood protection), e.g. against *Paecilomyces variotii*. In the case of seed treatment, from 0.001 to 50 g, preferably from 0.01 to 10 g, of active ingredient are required per kilogram of seed.

The agents or ready-to-use formulations produced therefrom, such as solutions, emulsions, suspensions, powders, dusts, pastes or granules, are applied in a known manner, for example by spraying, atomizing, dusting, broadcasting, dressing or pouring.

Examples of such formulations are:

I. 90 parts by weight of compound No. 1 are mixed with 10 parts by weight of N-methyl-α-pyrrolidone to give a solution which is suitable for use in the form of very small drops.

II. 20 parts by weight of compound No. 5 are dissolved in a mixture which consists of 80 parts by weight of xylene, 10 parts by weight of the adduct of from 8 to 10 moles of ethylene oxide with 1 mole of oleic acid N-monoethanolamide, 5 parts by weight of the calcium salt of dodecylbenzenesulfonic acid and 5 parts by weight of the adduct of 40 moles of ethylene oxide with 1 mole of castor oil. By pouring the solution into water and finely distributing it therein, an aqueous dispersion is obtained.

III. 20 parts by weight of compound No. 1 are dissolved in a mixture which consists of 40 parts by weight of cyclohexanone, 30 parts by weight of isobutanol and 20 parts by weight of the adduct of 40 moles of ethylene oxide with 1 mole of castor oil. By pouring the solution into water and finely distributing it therein, an aqueous dispersion is obtained.

IV. 20 parts by weight of compound No. 5 are dissolved in a mixture which consists of 25 parts by weight of cyclohexanol, 65 parts by weight of a mineral oil fraction boiling within a range from 210° to 280° C. and 10 parts by weight of the adduct of 40 moles of ethylene oxide with 1 mole of castor oil. By pouring the solution into water and finely distributing it therein, an aqueous dispersion is obtained.

V. 80 parts by weight of compound No. 1 are thoroughly mixed with 3 parts by weight of the sodium salt of diisobutylnaphthalene-α-sulfonic acid, 10 parts by weight of the sodium salt of a ligninsulfonic acid from a sulfite waste liquor and 7 parts by weight of silica gel powder, and the mixture is milled in a hammer mill. By finely distributing the mixture in water, a spray liquor is obtained.

VI. 3 parts by weight of compound No. 5 are thoroughly mixed with 97 parts by weight of finely divided kaolin. A dusting agent which contains 3% by weight of the active ingredient is obtained in this manner.

VII. 30 parts by weight of compound No. 1 are thoroughly mixed with a mixture consisting of 92 parts by weight of silica gel powder and 8 parts by weight of liquid paraffin, which has been sprayed onto the surface of this silica gel. A formulation of the active ingredient having good adhesion is obtained in this manner.

VIII. 40 parts by weight of compound No. 5 are thoroughly mixed with 10 parts by weight of the sodium salt of a phenolsulfonic acid/urea/formaldehyde condensate, 2 parts by weight of silica gel and 48 parts by weight of water. A stable aqueous dispersion is obtained. An aqueous dispersion is obtained by dilution with water.

IX. 20 parts by weight of compound No. 1 are thoroughly mixed with 2 parts by weight of the calcium salt of dodecylbenzenesulfonic acid, 8 parts by weight of a fatty alcohol polyglycol ether, 2 parts by weight of the sodium salt of a phenolsulfonic acid/urea/formaldehyde condensate and 68 parts by weight of a paraffinic mineral oil. A stable oily dispersion is obtained.

In these application forms, the novel agents may also be present together with other active ingredients, for example herbicides, insecticides, growth regulators and fungicides, or may be mixed with fertilizers and applied together with them. Mixing with fungicides results, in many cases, in an extension of the fungicidal action spectrum.

USE EXAMPLES

The comparative active ingredient used was α-(4-chlorophenyl)-α-cyclopropyl-3-pyridinemethanol (known from U.S. Pat. No. 3,396,224).

USE EXAMPLE 1

Activity against *Plasmopara viticola*

Leaves of "Müller Thurgau" pot vines were sprayed with an aqueous spray liquor containing 80% of active ingredient and 20% of emulsifier, the percentages being based on the dry substance. In order to allow assessment of the durational action of the active ingredients, the plants were placed in a greenhouse for 8 days after the spray coating had dried. Only then were the leaves infected with a zoospore suspension of *Plasmopara viticola* (vine peronospora). The vines were then placed in a water vapor-saturated chamber at 24° C. for 48 hours and then in a greenhouse at from 20° to 30° C. for 5 days. After this time, the plants were returned to the moist chamber for 16 hours in order to accelerate eruption of the sporangia carrier. The extent of fungal development on the underside of the leaves was then assessed.

The result shows that active ingredients 1 and 5, when applied as a 0.025% strength (% by weight) spray liquor, have a better fungicidal action (90%) than the known comparative ingredient A (60%).

USE EXAMPLE 2

Activity against *Botrytis cinerea* on peppers

Pepper seedlings of the Neusiedler Ideal Elite variety, after 4 or 5 leaves were well developed, were sprayed to run-off with aqueous suspensions containing 80% of active ingredient and 20% of emulsifier, the percentages being based on the dry substance. After the treated plants had been cultured for 8 days in a greenhouse, they were inoculated with a spore suspension of *Botrytis cinerea* containing $1.7 \times 10^6$ spores/ml in a 2% strength biomalt solution. They were then placed in a controlled-climate chamber at 22°–24° C. and high atmospheric humidity. After 5 days, the extent of fungal development could be evaluated. (Fungal attack on the leaf surfaces).

The result shows that active ingredient 1, when applied at a 0.025% strength spray liquor, has a better fungicidal action (100%) than the known comparative active ingredient A (75%).

We claim:

1. A compound selected from the group consisting of those of the formula 1

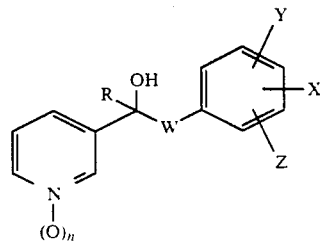

where R is selected from the group consisting of unsubstituted and $C_1$–$C_4$-alkyl-substituted cyclopropyl, cyclopentyl, cyclohexyl, cycloheptyl, and cyclooctyl, and unsubstituted and $C_1$–$C_4$-alkyl-substituted $C_3$–$C_8$-cycloalkenyl, X, Y, and Z, independently of one another, are selected from the group consisting of hydrogen, halogen, $C_1$–$C_4$-alkyl, $C_1$–$C_4$-alkoxy, $C_1$–$C_4$-alkoximino, halo-$C_1$–$C_4$-alkyl, cyano, nitro, unsubstituted and halogen-substituted phenyl, and unsubstituted and halogen-substituted phenoxy, W is selected from the group consisting of —CH$_2$— and —CH$_2$CH$_2$—, and n is 0 or 1, and plant-tolerated acid-addition salts thereof.

2. A fungicidal composition containing a solid or liquid carrier and a fungicidally effective amount of a compound selected from the group consisting of those of the formula 1

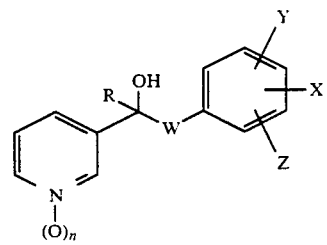

where R is selected from the group consisting of unsubstituted and $C_1$–$C_4$-alkyl-substituted cyclopropyl, cyclopentyl, cyclohexyl, cycloheptyl, and cyclooctyl, and unsubstituted and $C_1$–$C_4$-alkyl-substituted $C_3$–$C_8$-cycloalkenyl, X, Y, and Z, independently of one another, are selected from the group consisting of hydrogen, halogen, $C_1$–$C_4$-alkyl, $C_1$–$C_4$-alkoxy, $C_1$–$C_4$-alkoximino, halo-$C_1$–$C_4$-alkyl, cyano, nitro, unsubstituted and halogen-substituted phenyl, and unsubstituted and halogen-substituted phenoxyl, W is selected from the group consisting of —CH$_2$— and —CH$_2$CH$_2$—, and n is 0 or 1, and plant-tolerated acid-addition salts thereof.

3. A process for controlling fungi, which comprises allowing a fungicidally effective amount of a compound selected from the group consisting of those of the formula 1

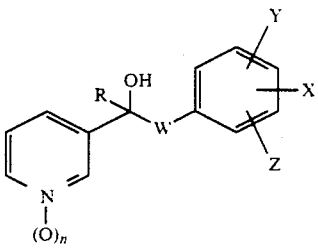

where R is selected from the group consisting of unsubstituted and C$_1$-C$_4$-alkyl-substituted cyclopropyl, cyclopentyl, cyclohexyl, cycloheptyl, and cyclooctyl, and unsubstituted and C$_1$-C$_4$-alkyl-substituted C$_3$-C$_8$-cycloalkenyl, X, Y, and Z, independently of one another, are selected from the group consisting of hydrogen, halogen, C$_1$-C$_4$-alkyl, C$_1$-C$_4$-alkoxy, C$_1$-C$_4$-alkoximino, halo-C$_1$-C$_4$-alkyl, cyano, nitro, unsubstituted and halogen-substituted phenyl, and unsubstituted and halogen-substituted phenoxy, W is selected from the group consisting of —CH$_2$— and —CH$_2$CH$_2$—, and n is 0 or 1, and plant-tolerated acid-addition salts thereof, to act on the fungi or on the materials, plants, seed or soil threatened by fungal attack.

4. A compound of the formula 1 as claimed in claim 1, wherein R is cyclopropyl, X, Y and Z are 2,4-dichloro, W is —CH$_2$— and n is 0.

5. A compound of the formula 1 as claimed in claim 1, wherein R is cyclopropyl, X, Y and Z are 2-chloro, W is —CH$_2$— and n is 0.

6. A compound according to claim 1, wherein R is selected from the group consisting of C$_3$-C$_8$-cycloalkenyl and C$_1$-C$_4$-alkyl-substituted C$_3$-C$_8$-cycloalkenyl.

7. A compound of claim 1, wherein R is cyclopropyl.

8. A compound of claim 1, wherein R is cyclopropyl, X, Y and Z are 4-chloro, W is —CH$_2$— and n is 0.

* * * * *